United States Patent [19]

Durant et al.

[11] 4,126,670

[45] Nov. 21, 1978

[54] METHOD OF STIMULATING HISTAMINE $H_2$-RECEPTORS

[75] Inventors: Graham J. Durant; Charon R. Ganellin, both of Welwyn Garden City; Michael E. Parsons, St. Albans, all of England

[73] Assignee: Smith Kline & French Laboratories Limited, Welwyn Garden City, England

[21] Appl. No.: 780,950

[22] Filed: Mar. 24, 1977

[30] Foreign Application Priority Data

Mar. 29, 1976 [GB] United Kingdom ............... 12476/76

[51] Int. Cl.$^2$ ..................... A61K 29/00; A61K 31/17; G01N 33/16

[52] U.S. Cl. .......................................... 424/9; 424/322

[58] Field of Search ..................................... 424/9, 322

[56] References Cited

U.S. PATENT DOCUMENTS 3,116,327  12/1963  Kartinos .............................. 260/564

OTHER PUBLICATIONS

Doherty, JACS, vol. 79, 1957, pp. 5667–5671.
Black, Nature, vol. 236, 1972, pp. 385–390.
Durant, J. Med. Chem., vol. 18, 1975, pp. 905–909.

*Primary Examiner*—Anna P. Fagelson
*Attorney, Agent, or Firm*—Joan S. Keps; Richard D. Foggio; William H. Edgerton

[57] ABSTRACT

S-[3-(Dialkylamino)propyl]isothioureas which are specific histamine $H_2$-agonists.

6 Claims, No Drawings

METHOD OF STIMULATING HISTAMINE H₂-RECEPTORS

This invention relates to a novel method for selectively stimulating histamine H₂-receptors by administering S-[3-(dialkylamino)propyl]isothioureas which are specific histamine H₂-receptor agonists.

Pharmaceutical compositions comprising salts of S-[3-(dimethylamino)propyl]isothiourea are disclosed and are described as being useful in inducing hypotensive conditions in laboratory animals in U.S. Pat. No. 3,116,327.

The preparation of S-[3-(diethylamino)propyl]isothiourea as a potential anti-irradiation agent has been described by D. G. Doherty et al. (J. Amer. Chem. Soc. 79 5667 (1957)).

Histamine H₂-receptor agonists have been defined by Black et al. (Nature 236, 385 (1972)). These compounds may be used for example as diagnostic agents to detect achlorhydria and to test the acid secretory capacity of the stomach. When this test is carried out using histamine, a histamine H₁-receptor antagonist (such as mepyramine or chlorpheniramine) is usually also administered to block the H₁-activity of histamine. This method may give rise to distressing side effects such as skin flushing, nausea, abdominal cramps, headache, dizziness and hypotension.

One example of a selective histamine H₂-agonist is 4-methylhistamine (Durant et al., J. Med. Chem. 18,905 (1975)). It is an object of the present invention to provide a method of testing which uses pharmaceutical compounds which are more selective in their pharmacological actions.

According to the present invention we provide a method of selectively stimulating histamine H₂-receptors which comprises administering to an animal, in an effective amount, a pharmaceutically acceptable salt of a compound of Formula 1:

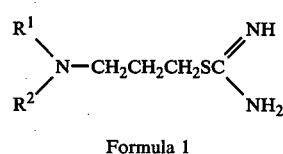

Formula 1 wherein $R^1$ and $R^2$ which may be the same or different are methyl or ethyl.

The active ingredients of the methods of this invention will normally exist as the acid addition salts but, for convenience, reference will be made throughout this specification to the parent compounds.

Compounds of Formula 1 may be prepared according to the following scheme:

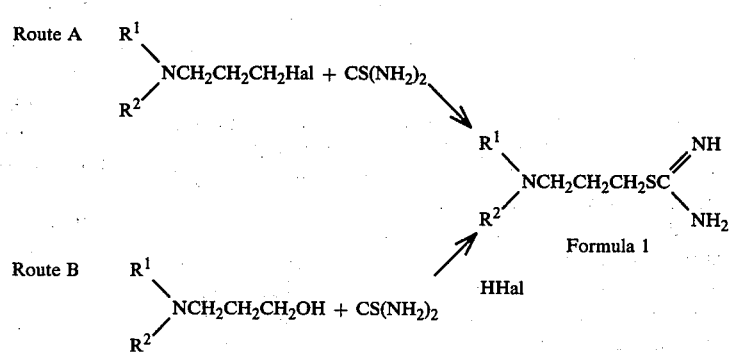

In route A a dialkylaminopropyl halide is reacted with thiourea at an elevated temperature, preferably between 70° C. and 140° C. Preferably this reaction is carried out in a suitable polar solvent, such as ethanol or isopropanol. In Route B a dialkylaminopropyl alcohol and thiourea are heated together in the presence of a suitable acid, such as hydrobromic acid. Preferably this reaction is carried out at an elevated temperature e.g., about 125° C.

Acid addition salts of compounds of Formula 1 may be converted into other acid addition salts by use of ion-exchange resins, such as Amberlite IRC-50.

We have discovered that the compounds of Formula 1 are potent histamine H₂-receptor agonists, the characterisation of which is explained in detail by Black et al., Nature 1972, 236, 385. At the same time, because of their selectivity, the compounds of Formula 1 possess very little histamine H₁-receptor agonist activity, the ratio of H₂- and H₁- agonist activity relative to histamine being at least 1000 to 1.

The histamine-like activity of the compounds of Formula 1 may be demonstrated by the following tests (see Black et al. Nature 1972, 236, 385):

1. Histamine H₂-agonist activity
   (a) stimulation of secretion of gastric acid from the perfused stomachs of rats anaesthetised with urethane. The compounds of Formula 1 show activity when given intravenously at a dose range of 0.5 to 50 micromoles per kilogram
   (b) stimulation of secretion of gastric acid in the Heidenhain pouch dog
   (c) inhibition of evoked contractions of the rat uterus
   (d) increased rate of beating of guinea-pig right atrium.
   (e) stimulation of secretion of gastric acid in cats anaesthetised with sodium pentobarbitone.
2. The lack of histamine H₁-agonist activity may be demonstrated by measuring contractions of an isolated piece of guinea-pig ileum (which are normally evoked by histamine).

Typical results for S-[3-dimethylamino)propyl]isothiourea are expressed below as a percentage of the corresponding activity of histamine:

| Preparation | Agonist Activity (mean with 95% confidence limits) |
| --- | --- |
| Rat Gastric Secretion | 19.5 (13.9–26.8) |
| Dog Heidenhain pouch | 58 |
| Rat Uterus | 17.5 (14.4–21.2) |
| Guinea-pig atrium | 70.7 (60.8–81.2) |

| Preparation | Agonist Activity (mean with 95% confidence limits) |
|---|---|
| Cat Gastric Secretion | 400–500 |
| Guinea-pig ileum | <0.0001 |

The histamine $H_2$-receptor agonist activity of S-[3-(dimethylamino)propyl]isothiourea was inhibited by the histamine $H_2$-receptor antagonist, metiamide. S-[3-(Dimethylamino)propyl]isothiourea has no significant agonist activity on catecholamine $\beta$-receptors in the guinea pig atrium and muscarinic cholinergic receptors in the guinea pig ileum. In the methods of this invention the compounds of Formula 1 may be administered in pharmaceutical compositions comprising an effective amount of a compound of Formula 1 in the form of a pharmaceutically acceptable acid addition salt, together with a pharmaceutical carrier. Such addition salts include those with hydrochloric, hydrobromic, hydriodic, sulphuric and maleic acids. Each dosage unit will suitably contain the active ingredient in an amount of from about 10 mg to about 200 mg, preferably from about 50 mg to about 100 mg.

The methods of selectively stimulating $H_2$-histamine receptors and of diagnosis for testing the secretory capacity of the stomach, according to this invention, comprise administering to an animal a compound of Formula 1. These compounds will usually be administered in the form of a pharmaceutically acceptable acid addition salt. The compounds will preferably be administered in dosage unit form as described hereabove. Preferably compounds of Formula 1 will be administered by intravenous or subcutaneous injection.

The dose level for testing the secretory capacity of the stomach, according to this invention, is an intravenous injection of about 1 mg/kg of a compound of Formula 1, an intravenous infusion of about 500 $\mu$g/kg/min of a compound of Formula 1 or a subcutaneous injection of about 800 $\mu$g/kg of a compound of Formula 1.

The invention is illustrated by the following examples, wherein temperatures are given in degrees centigrade.

EXAMPLE 1

S-[3-(Dimethylamino)propyl]isothiourea dihydrochloride (a) 3-(Dimethylamino)-1-chloropropane hydrochloride (79 g) in ethanol (300 ml) was added over a period of 5 mins to a mixture of thiourea (38 g) in ethanol (500 ml). The resultant mixture was boiled under reflux and ethanol (100 ml) was removed by distillation. Further quantities of 3-(dimethylamino)-1-chloropropane hydrochloride (8 g and 4 g) were added after 30 hrs and 54 hrs. refluxing. After the mixture had boiled under reflux for a total of 78 hours the solvent was removed by evaporation to give a moist solid which was filtered off and recrystallised from methanol/isopropanol to give the title product (92.9 g, 79%) m.p. 160.5°–161.5°.

(b) Equimolar quantities of thiourea and 3-(dimethylamino)-1-chloropropane hydrochloride and a little ethanol are heated together at 140° for 3 hours, and the cooled mixture is recrystallised from methanol/isopropanol to give the title product.

EXAMPLE 2

S-[3-(Diethylamino)propyl]isothiourea dihydrobromide

A mixture of 3-(diethylamino)propyl alcohol (65.5 g), thiourea (38.0 g) and aqueous hydrobromic acid (48%, 25 ml) was boiled under reflux for 17 hours, and evaporated to dryness. The residue was triturated with ethanol and recrystallised from ethanol/methanol to give the title product, m.p. 125°–127° which was further recrystallised from absolute ethanol to give a 10.0 g sample with m.p. 144°–145°.

EXAMPLE 3

S-[3-(Ethylmethylamino)propyl]isothiourea dihydrochloride

When 3-(ethylmethylamino)-1-chloropropane hydrochloride is substituted for 3-(dimethylamino)-1-chloropropane hydrochloride in the procedure of Example 1, the title compound is prepared. 3-(Ethylamethylamino)-1-chloropropane hydrochloride may be prepared by treating 3-(ethylmethylamino)-propan-1-ol with thionyl chloride.

EXAMPLE 4

3-(Ethylmethylamino)propylisothiourea dihydrobromide

When 3-(ethylmethylamino)propyl alcohol is substituted for 3-(diethylamino)propyl alcohol in the procedure of Example 2, the title compound is prepared.

The following examples illustrate the incorporation of compounds of Formula 1 into pharmaceutical compositions and are not to be considered as limiting the invention set forth in the claims appended hereto:

EXAMPLE 5

By dissolving 70 mg of S-[3-diethylaminopropyl]isothiourea hydrochloride in 2 ml of sterile water or normal saline solution, a pharmaceutical composition suitable for parenteral administration is prepared.

EXAMPLE 6

By dissolving 20 mg of S-[3-diethylaminopropyl]isothiourea hydrochloride in 2 ml of sterile water or normal saline solution, a pharmaceutical composition suitable for parenteral administration is prepared.

What we claim is:

1. A method of selectively stimulating histamine $H_2$-receptors which comprises administering a pharmaceutically acceptable salt of a compound of the formula:

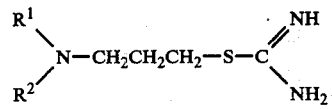

wherein $R^1$ and $R^2$ which may be the same or different are methyl or ethyl, to an animal in an amount sufficient to stimulate said receptor.

2. A method of diagnosing gastric secretory capacity which comprises administering a pharmaceutically acceptable salt of compound of the formula:

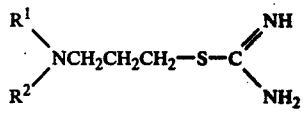

wherein $R^1$ and $R^2$, which may be the same or different, are methyl or ethyl, internally to an animal in an amount sufficient to test the gastric secretory activity and to detect achlorhydria.

3. A method of claim 1 wherein $R^1$ and $R^2$ are both methyl.

4. A method of claim 2 wherein $R^1$ and $R^2$ are both methyl.

5. A method of claim 1 wherein $R^1$ and $R^2$ are both ethyl.

6. A method of claim 2 wherein $R^1$ and $R^2$ are both ethyl.

* * * * *